(12) United States Patent
Zandona et al.

(10) Patent No.: US 8,540,713 B2
(45) Date of Patent: Sep. 24, 2013

(54) CLAMP FOR TEMPORARY OR DEFINITIVE EXTERNAL ORTHOPAEDIC FIXATION, AND EXTERNAL FIXATION SYSTEM COMPRISING SAID CLAMP

(75) Inventors: Enrico Zandona, Verona (IT); Denis Lorenzini, Caprino Veronese (IT); Daniele Venturini, Povegliano Veronese (IT); Selvadurai Nayagam, Liverpool (GB); Marco Assom, Rivoli-Torino (IT)

(73) Assignee: Orthofix S.r.l. (IT)

( * ) Notice: Subject to any disclaimer, the term of this patent is extended or adjusted under 35 U.S.C. 154(b) by 0 days.

(21) Appl. No.: 13/370,980

(22) Filed: Feb. 10, 2012

(65) Prior Publication Data
US 2012/0209264 A1  Aug. 16, 2012

Related U.S. Application Data

(60) Provisional application No. 61/441,953, filed on Feb. 11, 2011.

(51) Int. Cl.
*A61B 17/00* (2006.01)
*A61F 4/00* (2006.01)
*A61F 5/04* (2006.01)

(52) U.S. Cl.
USPC ............................................ 606/54; 606/324

(58) Field of Classification Search
USPC ........................ 606/53–59, 324, 250–253, 278
See application file for complete search history.

(56) References Cited

U.S. PATENT DOCUMENTS

| | | |
|---|---|---|
| 4,978,348 A | 12/1990 | Ilizarov |
| 5,752,954 A | 5/1998 | Mata et al. |
| 2002/0165543 A1 | 11/2002 | Winquist et al. |
| 2003/0181911 A1 | 9/2003 | Venturini |
| 2007/0038217 A1* | 2/2007 | Brown et al. ................... 606/57 |
| 2008/0247818 A1 | 10/2008 | Oesch et al. |
| 2009/0326532 A1 | 12/2009 | Schulze |
| 2010/0298827 A1 | 11/2010 | Cremer et al. |

FOREIGN PATENT DOCUMENTS

DE    9005149 U1   7/1990

OTHER PUBLICATIONS

International Search Report issued in connection with PCT/EP2011/004549.

* cited by examiner

*Primary Examiner* — Eduardo C Robert
*Assistant Examiner* — Christina Negrellirodriguez
(74) *Attorney, Agent, or Firm* — Akerman Senterfitt

(57) ABSTRACT

A clamp applicable to both temporary and definitive orthopaedic external fixation systems comprising a first coupling element having a pair of opposite jaws defining one or more seats to house a first component of the orthopaedic external fixation system. A second coupling element comprises a pair of opposite jaws defining one or more seats to house a second component of the orthopaedic external fixation system. An interconnection pin passes through and connects the first and second coupling elements along an axis of rotation. A fastening means is arranged to bring the clamp from a slack configuration. The first and second coupling elements are relatively rotatable along the axis of rotation to a locked configuration, and are relatively rotatable with each other. These fastening means include manually operable temporary fastening means to temporarily lock the clamp, and definitive fastening means operable with a fastening tool, to definitively lock the clamp.

16 Claims, 11 Drawing Sheets

CLAMP FOR TEMPORARY OR DEFINITIVE EXTERNAL ORTHOPAEDIC FIXATION, AND EXTERNAL FIXATION SYSTEM COMPRISING SAID CLAMP

CROSS-REFERENCE TO RELATED APPLICATIONS

This application claims priority to U.S. Provisional Patent Application No. 61/441,953 filed Feb. 11, 2011, the disclosure of which is hereby incorporated by reference.

FIELD OF APPLICATION

The present invention applies to the field of orthopaedic surgery and it relates in particular to a clamp intended for the temporary or definitive fixation of the elements composing an external fixation system.

The present invention also relates to an external fixation system comprising this clamp.

PRIOR ART

In orthopaedics, external fixation techniques for stabilizing, reducing and manipulating bone segments are known and commonly used. These techniques provide the surgical application of an external fixation system, composed in its simplest form of a set of rods associated by means of endosseous pins or Kirschner wires to the patient's bone structure. The articulation of rods with respect to each other and to fixators is carried out by suitable clamps.

These fixation systems can be applied temporarily during an operation, or definitively in order to be removed only upon full recovery from the treated pathological condition.

The use of temporary fixation systems is required especially for the following reasons:
- a patient may have serious lesions that require priority treatment;
- a patient may have lesions obliging interventions to be minimal;
- local conditions in the fracture region could preclude definitive fracture fixation owing to severe wound infection, or a lack of covering soft tissue, or a shortage of blood supply;
- single fractures to be treated may not be particularly serious, but they may require long and complex surgical interventions for their treatment if they are taken together with other fractures that have occurred.

In the latter case some or all of the fractures can be treated by means of external fixation systems. It is however necessary to avoid situations wherein one is forced to abandon fracture fixation: at the end of the primary treatment all long bones must be firmly fixed.

Beyond these specific requirements, external fixation systems are mainly applied in a definitive way. In the case of definitive fixation, however, a different performance is required of the external fixation system when compared to temporary applications. In particular, where an external fixation system for temporary application is above all required to present flexibility of use and rapidity of fixation, a system that is implanted in a definitive way must ensure a certain degree of rigidity (see for example Orthofix's device marketed under the name XCaliber, which allows for adjustment of lateral curvature while being able to beartorsional stress during the initial steps of treatment).

This stability partly derives from the alignment of the fixation system rods with the axes of the long bones to be treated, and partly from the intrinsic stiffness of the device itself and the number of screws, and furthermore partly in function of the geometrical configuration of the screws. A correct configuration will promote rapid healing and a quick recuperation of mobility.

Given the different requirements of the fixation system for these two applications, systems have been used up to now that are dedicated either to temporary treatment or to definitive treatment.

This specificity in treatment is undoubtedly one of the disadvantages of the external fixation systems known up to now; for example, when a temporary fixation needs to be applied that subsequently must be substituted by definitive fixation, it is necessary to replace the entire fixation system.

On the other hand, the main critical aspect that stands in the way of external fixation systems for mixed use is to do with the clamp that is intended to fasten joining elements such as rods, screws and Kirschner wires.

In fact, in cases of temporary fixation it is essential that this clamp allows the relative orientation of the elements it connects to be rapidly blocked, possibly without using a fastening tool. In definitive fixation, the blocking of the relative orientation must however be rigid and stable over time, features that clash with the above-mentioned fastening modes.

Therefore, the technical problem underlying the present invention is to provide a clamp that can be used in external fixation systems and that is suited for both temporary use and definitive use, i.e. that can be locked in a rapid and manual way, but that at the same time ensures rigidity and stability over time.

SUMMARY OF THE INVENTION

The above-mentioned technical problem is solved by a clamp for an external orthopaedic fixation system comprising:
- a first coupling element, comprising a pair of opposite jaws that together define one or more seats suitable for housing at least a first component of the external orthopaedic fixation system;
- a second coupling element, comprising a pair of opposite jaws that together define one or more seats suitable for housing at least a second component of the external orthopaedic fixation system;
- an interconnection pin crossing and connecting the first and second coupling elements along a main axis of rotation;
- fastening means arranged to bring the clamp from a slack configuration, wherein the first and second coupling elements are relatively rotatable at least along the main axis of rotation, to a locked configuration, wherein the first and second coupling elements are relatively integral with each other; these fastening means comprising in particular:
    - temporary fastening means, which can be manually operated, arranged to bring the clamp temporarily in a locked configuration;
    - definitive fastening means, which can be operated by means of a fastening tool, arranged to bring the clamp definitively in a locked configuration.

The alternative meanings "temporarily" and "definitively" are intended to discriminate, similarly to what has been done in the previous description of prior art, between a temporary fastening of the clamp components and a definitive fastening. The temporary, moderately tight fastening can be rapidly realized without using a fastening wrench; it allows the elements to be relatively fixed but it does not guarantee rigidity and stability of the chosen position over time. Instead the definitive fastening, which is stronger than the previous one, is able to withstand the regular stress that an external fixation system is exposed to in the course of a patient's treatment.

A person skilled in the art will immediately note how the presence of double fastening means on the clamp, the manual ones and those that are fastened by means of a tool, allows the device to be applied to external fracture fixation systems with the result that these systems will be suited for both temporary and definitive use.

Moreover it should be noted that, although the capabilities of the clamp according to the present invention are greatly adapted to the context of an external fixation system for both temporary and definitive use, this clamp can advantageously be used in any other orthopaedic application.

The above-mentioned temporary fastening means can advantageously comprise a fastening ring nut, arranged to fasten the first and second coupling elements to each other along the length of the clamp's interconnection pin.

In particular, the fastening ring nut can advantageously have a cylindrical peripheral handling surface that is conveniently knurled.

The single jaws of at least one of the pair of jaws can be both crossed by the interconnection pin, so that this pair of jaws is not fastened in the slack configuration of the clamp and fastened in the locked configuration of the clamp.

This configuration results in an advantageous acceleration of clamp locking operations, since the same means are used both to fasten the jaws and to fix the coupling elements.

The clamp can further comprise a spring interposed between the first and second coupling elements, which can advantageously determine a pre-fastening action of the jaws of the coupling element onto the respective seats.

In a first embodiment of the clamp according to the present invention, the fastening ring nut can engage a threaded end of the interconnection pin, the opposite end of said interconnection pin being constrained to the first coupling element, the second coupling element being interposed between the fastening ring nut and the first coupling element.

In alternative embodiments of the clamp, instead, the fastening ring nut is axially constrained to one end of the interconnection pin, the opposite end being threaded and engaging an at least partially threaded hole of the second coupling element, said first coupling element being interposed between the fastening ring nut and the second coupling element.

In one of these embodiments, which presents the advantage of great structural simplicity, the fastening ring nut even defines a fastening head that is integral with the interconnection pin, said definitive fastening means comprising a hollow in said head intended to allow it to receive a fastening tool.

In particular, the fastening ring nut can surround a connecting rod head of the interconnection pin, said definitive locking means comprising an eccentric body, rotatably mounted on the fastening ring nut which crosses said connecting rod head along an axis perpendicular to the main axis of rotation, the rotation of said eccentric body with respect to the fastening ring nut creating a translation of the end of the interconnection pin engaged in the second coupling element towards the fastening ring nut.

In some embodiments of the clamp, said definitive fastening means comprise an eccentric body, rotatably mounted on a hinging member that is axially integral with either one of the first and second coupling elements, said eccentric body crossing a connecting rod head of the interconnection pin along an axis perpendicular to the main axis of rotation, the opposite end of said interconnection pin being constrained to the other between the first and second coupling elements, the rotation of said eccentric body with respect to the hinging body promoting a translation of the opposite end of the interconnection pin towards said hinging body and a subsequent relative approach of the two coupling elements.

In one of these embodiments, the fastening ring nut is arranged in abutment against the outermost jaw of the second coupling element, said hinging body corresponding to the first coupling element, the end of the interconnection pin opposite the connecting rod head being threaded and constrained by screwing to the fastening ring nut.

In an alternative embodiment, said eccentric body hinges the first coupling element to the interconnection pin along a secondary axis of rotation, advantageously defining a second degree of rotational freedom between the first coupling element and the second coupling element in the slack configuration of the clamp.

The eccentric body can then be hinged onto a base portion that proceeds in the direction of the second coupling element as a protuberance of the innermost jaw of the first coupling element.

In this case, a central joint crossed by the interconnection pin can be advantageously arranged between the base portion and the second coupling element, said central joint having a sliding face along a concave periphery of the base portion and a flat face intended to couple with a surface of the internal jaw of the coupling element.

The above-identified technical problem is also solved by an external orthopaedic fixation system comprising at least one of the above-described clamps, besides known rods and fixators.

This external orthopaedic fixation system can further comprise at least an innovatively designed wire-carrier element, arranged to allow at least one Kirschner wire or other fixator of limited-diameter to be fixed onto one of the system clamps.

One should note that this wire-carrier element can also be advantageously applied outside the scope defined by the present invention, as it presents innovative features of its own.

The wire-carrier element can comprise a shank with a threaded portion onto which a fastening plate is screwed right up to an abutting plate that is integral with the shank.

The shank can comprise a gripping portion intended to be locked between the jaws of one of the system clamps.

The fastening plate can further advantageously have four peripheral teeth on one of its faces turned towards the abutting plate, equiangularly spaced along the circumference of said plate and arranged to abut against a flat surface of the abutting plate, thus defining, in collaboration with the shank portion comprised between the two plates, a seat for a Kirschner wire or for screws of limited diameter.

Further features and advantages will be apparent from the following description of some preferred, but not exclusive, embodiments of the present invention, with reference to the attached drawings, given by way of non-limiting examples.

DETAILED DESCRIPTION

Figure 1:
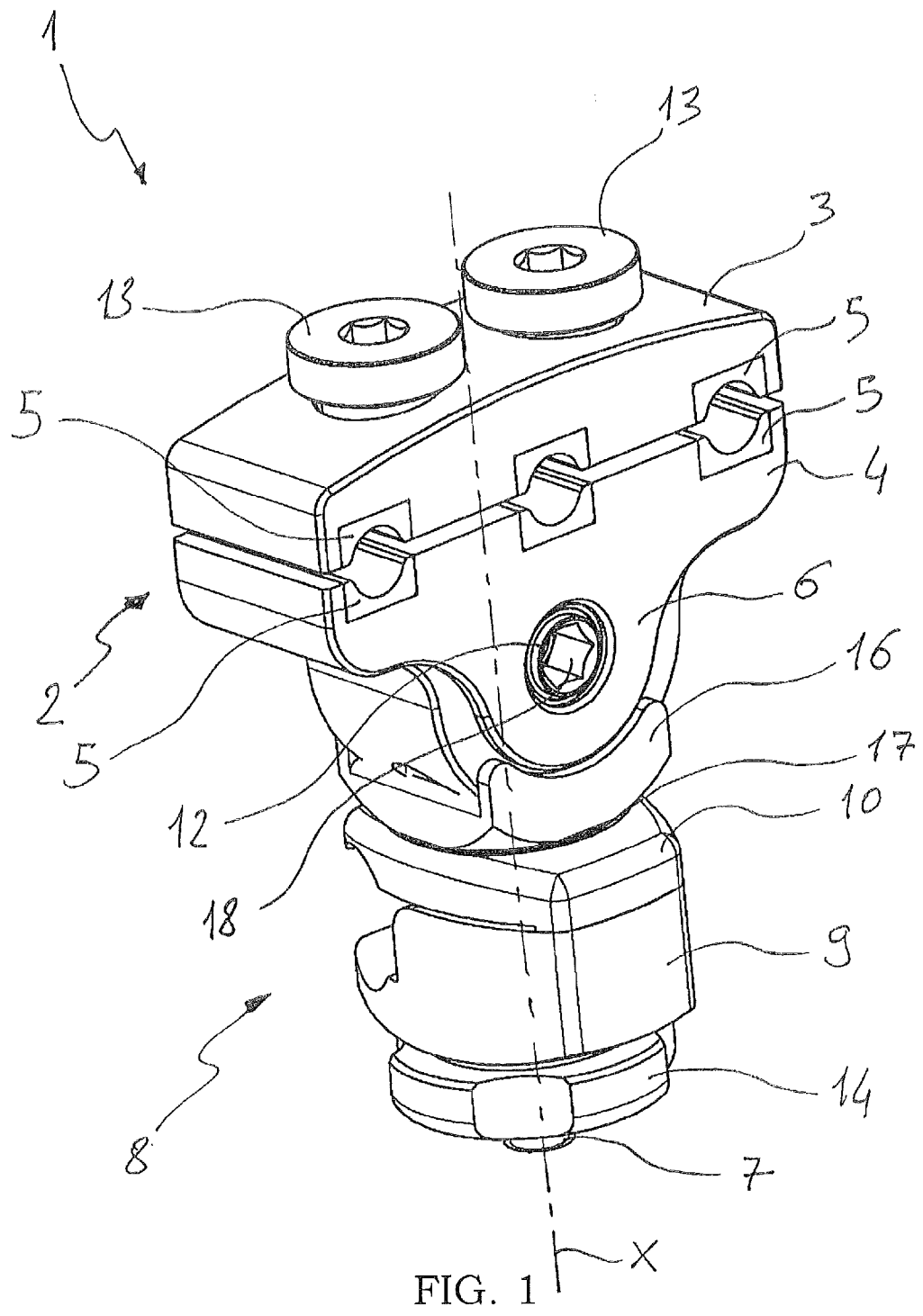
FIG. 1 is an axonometric view of a clamp according to the invention.
Figure 2:
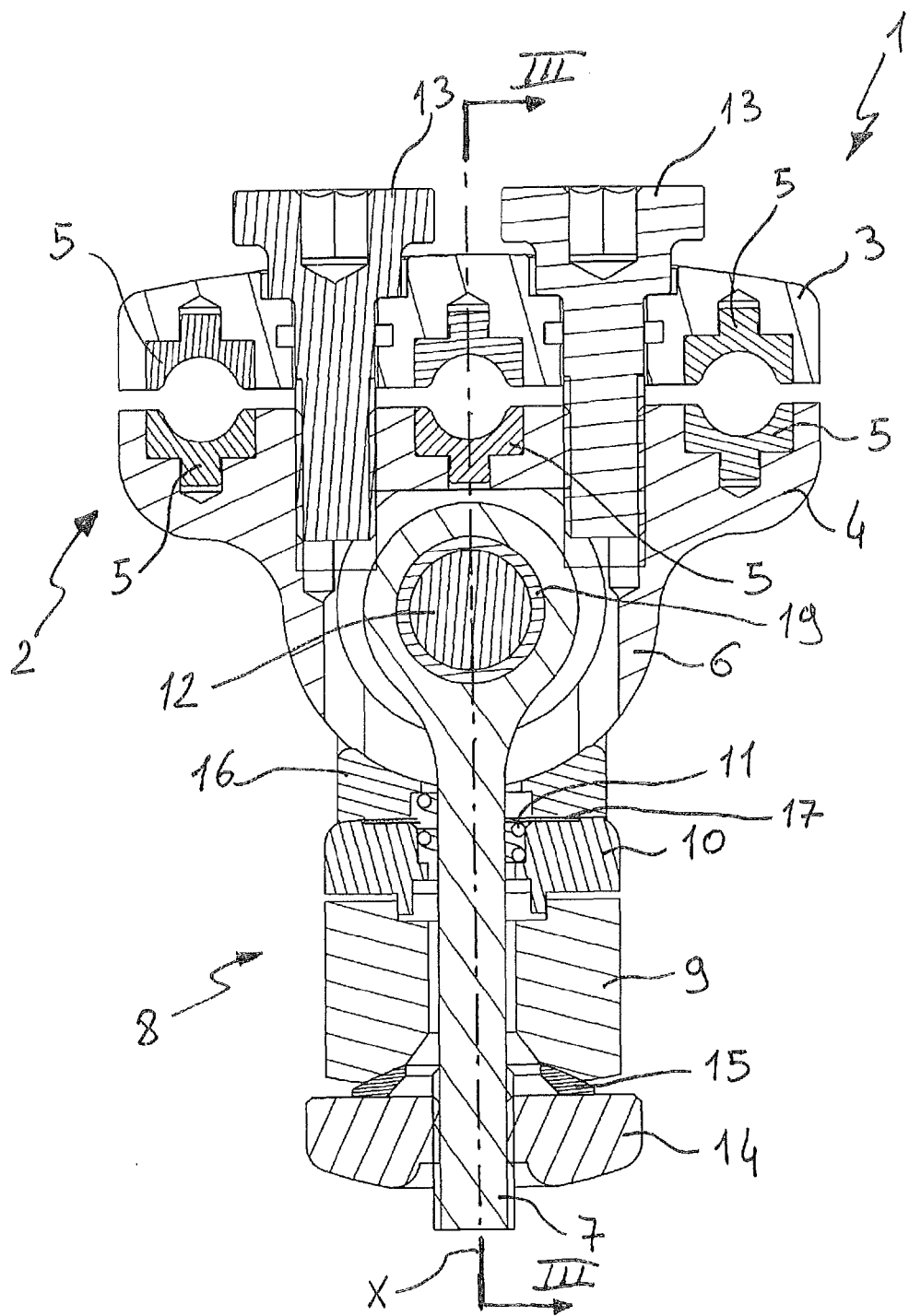
FIG. 2 is a sectional view along a vertical central plane of the clamp of FIG. 1.
Figure 3:
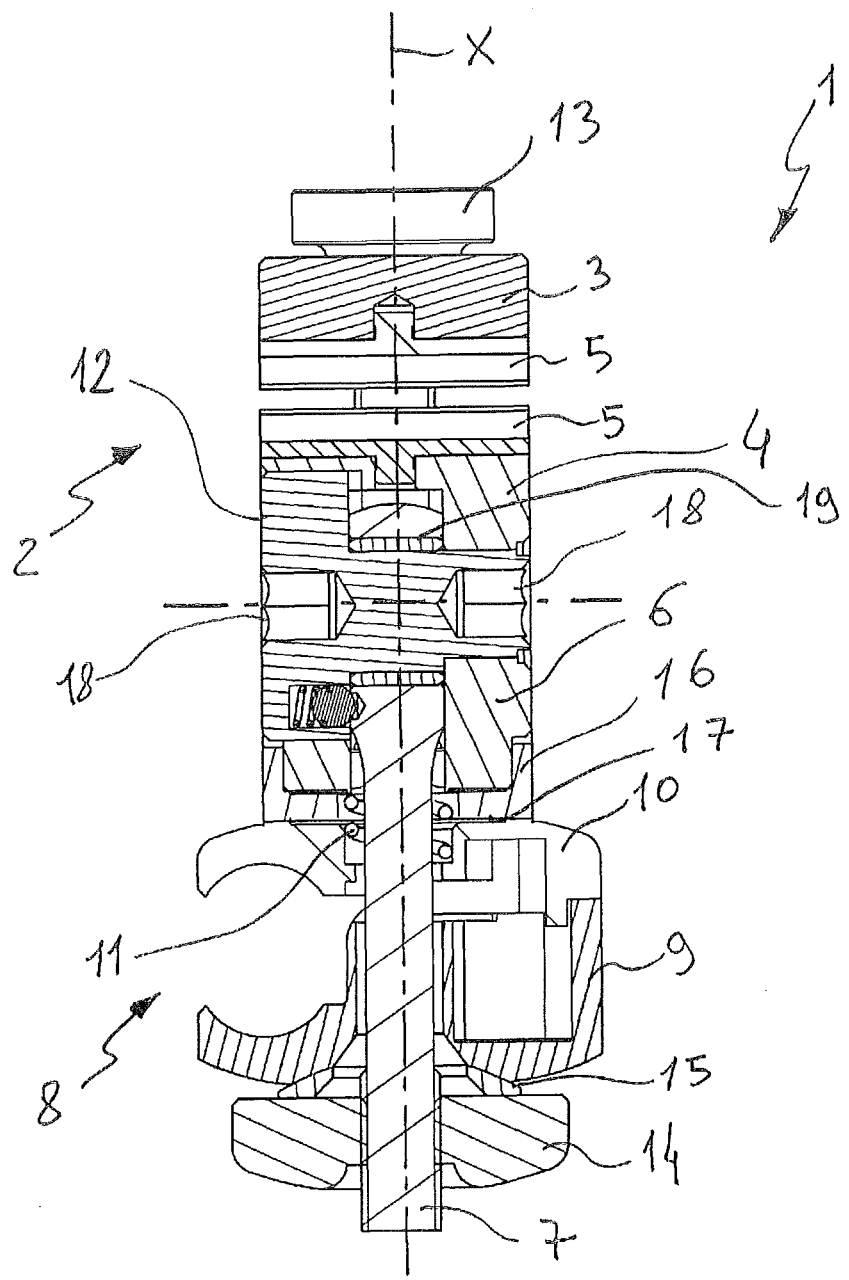
FIG. 3 is a sectional view, taken along the line of FIG. 2, of the clamp of FIG. 1.
Figure 4:
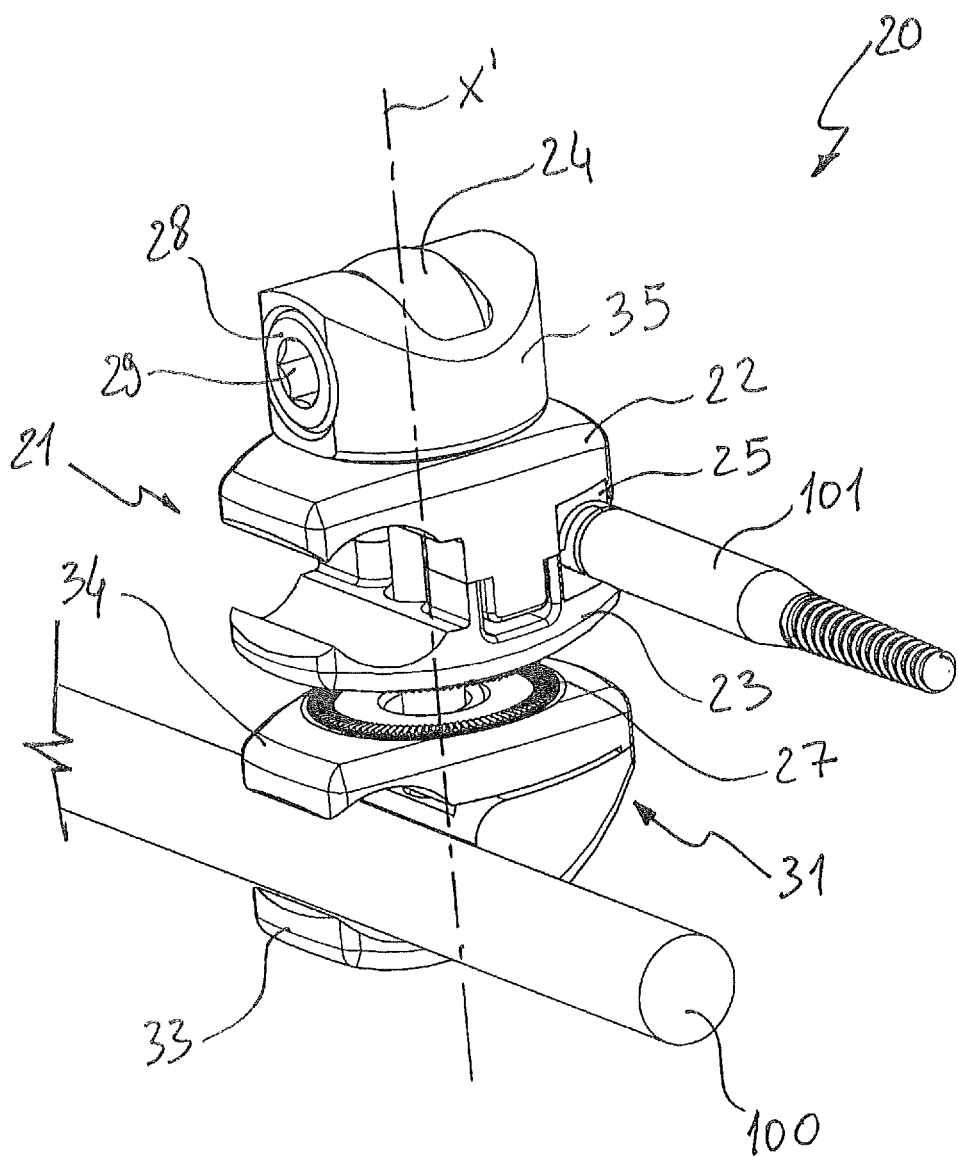
FIGS. 4 and 5 are respective axonometric views of a clamp according to an alternative embodiment of the present invention.
Figure 5:
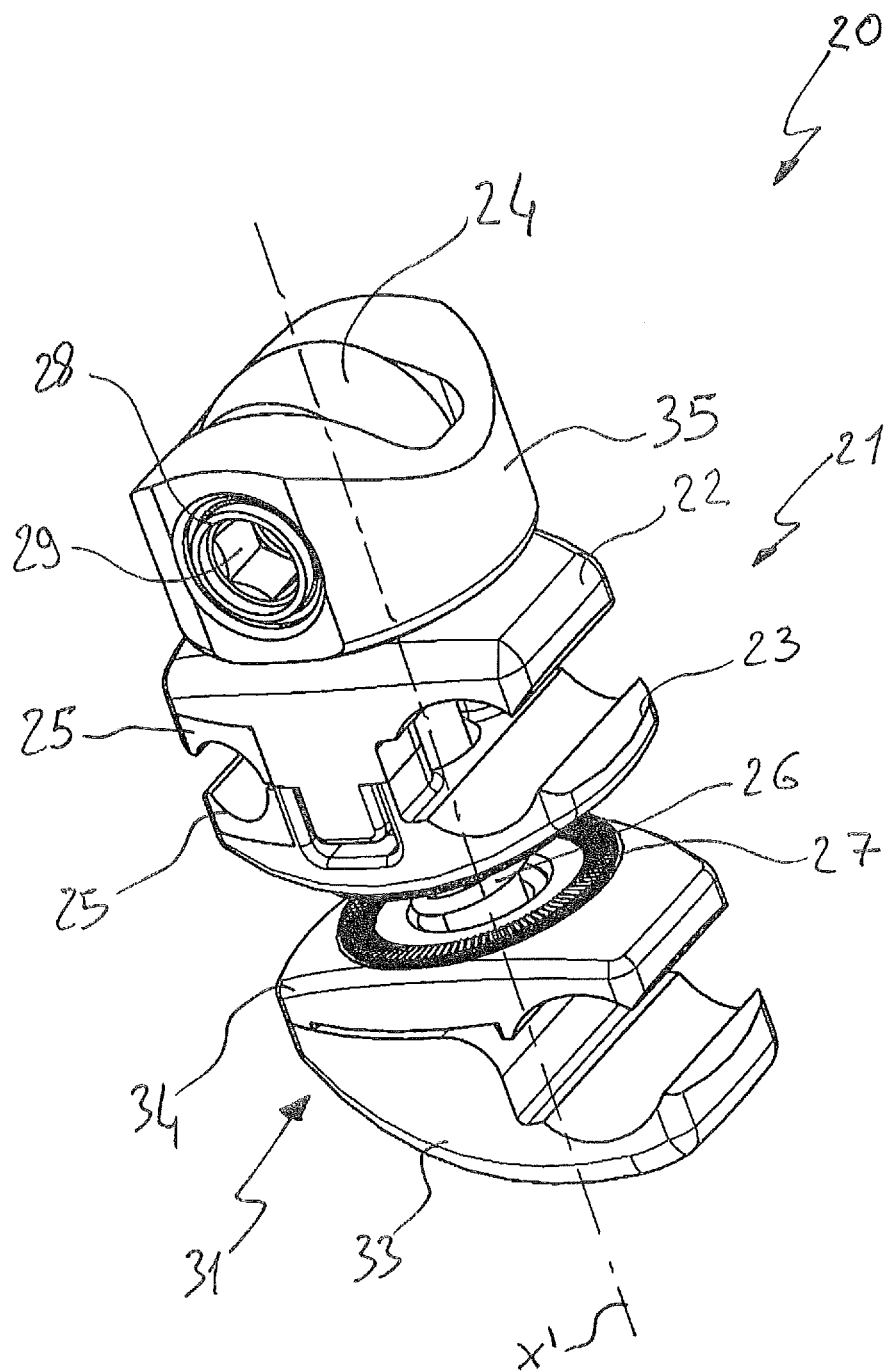
Figure 6:
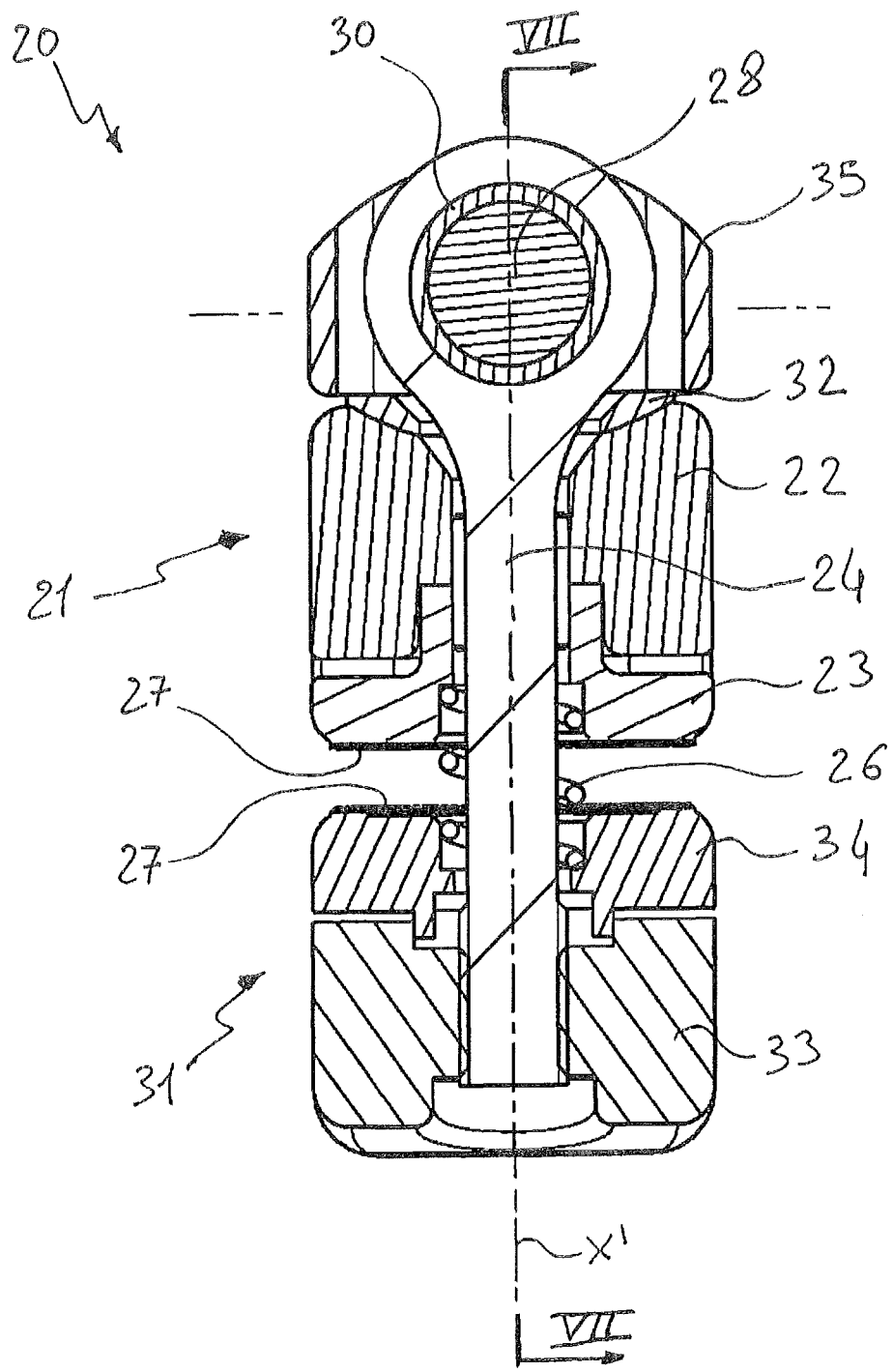
FIG. 6 is a sectional view along the line VI-VI of FIG. 7 of the clamp of FIGS. 4 and 5.
Figure 7:
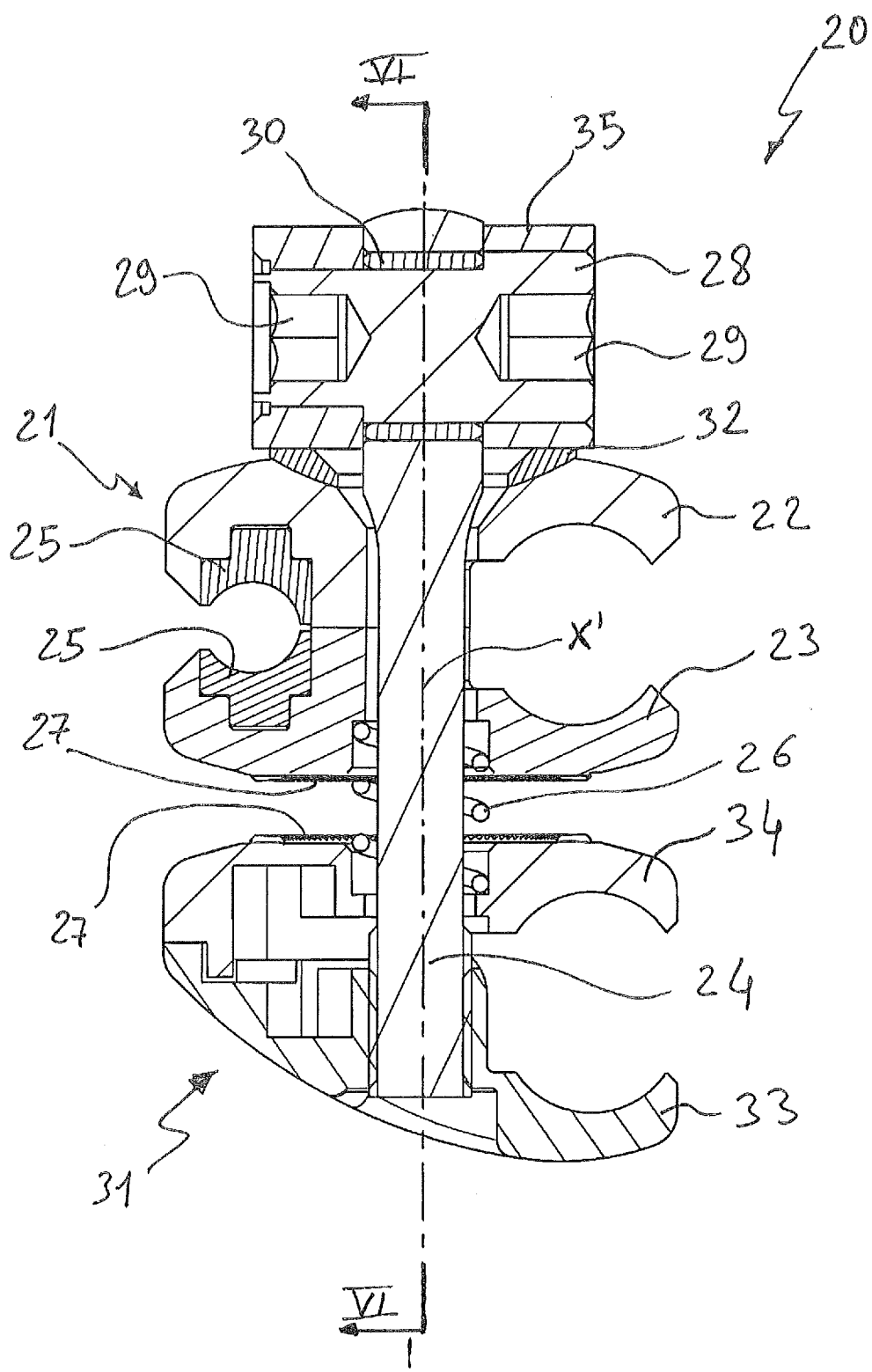
FIG. 7 is a sectional view, taken along the line VII-VII of FIG. 6, of the clamp of FIGS. 4 and 5.

According to a first embodiment of the present invention, FIGS. 1-3 show a first clamp, globally indicated with reference number 1, for an external modular fixation system suitable to be used for the treatment of lower limb bones, such as tibia, femur or pelvis. Through a simple dimensional adjustment it is possible to use this clamp also for upper limb bones, for example a humerus.

In this first embodiment, the clamp allows a rod and a plurality of endosseous pins to be fixed in a simple and stable way, as will be clear from the following description.

The clamp 1 comprises a first multi-seat coupling element 2 for fixing endosseous pins, comprising at least three seats to fasten as many endosseous pins.

The multi-seat coupling element 2 is preferably made of metal.

According to the present invention, the multi-seat coupling element 2 comprises an upper jaw 3 and a lower jaw 4. The upper jaw 3 performs the function of a lid and has a pair of through-holes, at least partially threaded, through which closing screws 13 pass. The lower jaw 4 comprises a corresponding pair of internally-threaded blind holes to receive the ends of the two screws 13.

At least an insert 5 is provided in at least one of the seats in order to fix the endosseous pins. In particular, the use of inserts of a hemispheric form is provided between the lower jaw 4 and the upper jaw 3 in order to define each housing seat of the endosseous pins.

These inserts 5 are made of a different material with respect to the jaws 3 and 4, for example out of a non-conductive material.

More particularly, it is preferable that these inserts are made of a radiotransparent material that is MRI-compatible.

In the example shown, the three seats are equidistant, the central seat is placed in correspondence with the central axis and the two remaining seats are on either side thereof.

A base portion 6 developing as a protuberance of the lower jaw 4 has a seat internally to house the head of an interconnection pin 7 shaped as a connecting rod with a shank extending along a main axis of rotation x, which is orthogonal to the seats defined by the first coupling element 2, towards a second rod coupling element 8.

The second rod coupling element 8 also has a lower jaw 9 and an upper jaw 10.

This second rod coupling element 8 has a single C-shaped seat, lateral and orthogonal with respect to the main axis of rotation x, for snap-fitting it to a fixing rod 100.

The lower and upper jaws 9, 10 of the second coupling element have a central through-hole through which the interconnection pin 7 passes.

A fastening ring nut 14, suitably knurled on the outside for better grip, is screwed on the free end of the interconnection pin 7. In particular, this ring nut 14 has a threaded central hole that is screwed on the end of said interconnection pin 7.

A washer 15 through which the interconnection pin 7 passes, is inserted between the lower jaw 9 of the second coupling element 8 and the ring nut 14.

In brief, the first multi-seat coupling element 2 is mounted onto the head of the interconnection pin 7. It is able to move freely and angularly, while the second rod coupling element 8 is rotatably mounted onto the interconnection pin 7.

A spring 11 is inserted between the first multi-seat coupling element 2 and the second rod coupling element 8 around the interconnection pin 7. This spring 11 is compressed between the lower jaw 4 of the first coupling element 2 and the upper jaw 10 of the second coupling element 8 and concealingly housed in impressions on the opposite surfaces of these jaws. The spring 11 defines a spring-loaded fastening force exerted by the jaws on the elements inserted into the seats of the coupling elements before locking the clamp.

Moreover, a central joint 16 with a central hole for the passage of the interconnection pin 7 is placed between the two coupling elements 2 and 3.

In order to avoid sliding during the usual assembly operations, respective anti-rotation means 17 are present on the surface of the upper jaw 10 of the second coupling element 8 and on the surface of the central joint 16; in the example these means are formed integrally with the body of the piece itself and they comprise a plurality of radially oriented grooves on a crown placed around the central hole.

Advantageously, the head of the interconnection pin 7 has a through-hole to allow an eccentric body 12 to be transversely inserted along a secondary axis of rotation y into a bush 19. This eccentric body 12 has, on the two opposite sides accessible from the outside, on the sides of the lower jaw 4 of the first coupling element 2, respective hollow socket heads 18 to receive a control socket wrench.

The simple rotation of the eccentric body 12 allows it to be locked in its seat and at the same time to bring the free end of the interconnection pin 7 nearer the first coupling element 2, thus defining a relative locking of the various elements of which clamp 1 is composed.

The clamp 1 can have a slack configuration in which the jaws of the second coupling element 8 are not fastened, the second coupling element 8 is rotatable with respect to the interconnection pin 7 along the main axis of rotation x and the axis of the interconnection pin 7 is rotatable with respect to the first coupling element 2 along the secondary axis of rotation y. In this slack configuration, therefore, two degrees of rotational freedom are present, together allowing for a proper relative positioning of the first coupling element 2 and the second coupling element 8. In alternative the clamp 1 can have a locked configuration in which the two coupling elements 2, 8 are relatively integral with each other and the jaws of the second coupling element 8 are fastened. It should be noted that the jaws of the first coupling element 2 are independent, since the fastening thereof is done by the closing screws 13 that are autonomous with respect to the interconnection pin 7.

The manual fastening of the fastening ring nut 14 allows the whole clamp 1 to be rapidly pre-closed with no need to use a wrench. This operation brings the clamp 1 from the slack configuration to a temporary locked configuration, which ensures the fastening of the jaws of the second coupling element and the relative locking of the two coupling elements, but does not ensure rigidity and stability over time of these conditions.

Then, in order to change to a definitive locked configuration, in which rigidity and stability over time are ensured, it is necessary to rotate the eccentric body 12 by means of a control socket wrench.

The clamp according to the first embodiment described above has several advantages, such as:
- the use of a single clamp to connect the rod and endosseous pins;
- the presence of two distinct degrees of rotational freedom for an easy relative positioning of the coupling elements;
- the option of manual pre-closure;
- the possibility to perform the fastening by a single rapid movement of the control wrench;
- the compatibility with MRI techniques.

When the clamp according to the first embodiment just described is used for upper limbs, it is possible to use the rod coupling element 8 in order to fix an endosseous pin, simply by changing the size of the various elements.

Therefore, where reference has been made to a rod coupling element, one should consider that this also comprises endosseous pin coupling elements.

According to a second embodiment of the present invention, FIGS. 4-7 show a second clamp, globally indicated with 20, suitable to be used for the treatment of lower limb bones, such as tibia, femur or pelvis. After a simple modification of the dimensions it is also possible to use this clamp for upper limb bones, for example humerus and forearm, as well as for treatments of the foot and ankle.

The second clamp comprises a first two-seat coupling element 21 comprising an upper jaw 22 and a lower jaw 23, both provided with a central through-hole for an interconnection pin 24 that extends along a main axis of rotation x'.

The two-seat coupling element 21 has, opposite each other on the two sides of the central hole, two open C-shaped seats to respectively house an endosseous pin and a rod. Again it is possible to adapt the dimensions of said opposite open seats, so that both seats are able to house a respective endosseous pin.

The open seats are therefore placed in an eccentric and orthogonal manner with respect to the main axis of rotation x'.

An insert 25 is provided between the upper jaw 22 and the lower jaw 23 on the jaw portion that is intended to house the endosseous pin.

This insert is made of a different material than the material used to realize the two-seat coupling element 21, in particular a non-conductive material, when the coupling element is preferably made of steel.

More particularly, it is preferable that this insert is made of a radiotransparent material that is MRI-compatible.

The clamp according to the second embodiment of the present invention further comprises a second coupling element 31 having a lower jaw 33 and an upper jaw 34.

This second coupling element has a single lateral C-shaped seat for clamping between the jaws.

These lower 33 and upper 34 jaws of the second coupling element 31 of the clamp 20 also have a central through-hole to allow the interconnection pin 24 to pass through.

This interconnection pin 24 has at its free end a threading that matches a corresponding internal threading that is present at least partially in the through-hole of the lower jaw 33 of the second coupling element 31.

In this manner the first two-seat coupling element 21 is rotatably mounted with respect to the interconnection pin 24, while the second coupling element 31 is rotatably constrained to the interconnection pin 24 to which it is screwed by means of its own lower jaw 33.

Basically the lower jaw 33 functions like a nut into which the entire second clamp 20 can be screwed.

A spring 26 is inserted between the first two-seat coupling element 21 and the second coupling element 31 around the interconnection pin 24. This spring 26 is compressed between the lower jaw 23 of the first two-seat coupling element 21 and the upper jaw 34 of the second coupling element 31, and concealingly housed in impressions on the opposite surfaces of these jaws. The spring defines a spring-loaded fastening force exerted by the jaws on the elements inserted into the seats of the coupling elements before locking the clamp.

In order to avoid sliding during the usual assembly operations, respective anti-rotation means 27 are present on the opposite surfaces of the upper jaw 34 of the second coupling element 31 and of the lower jaw 23 of the first coupling element 21; in the example these means are formed integrally with the body of the piece itself and they comprise a plurality of radially oriented grooves on a crown placed around the central hole.

Advantageously, the end of the interconnection pin 24 opposite the one that is screwed on the second coupling element 31 has an enlargement with the shape of a connecting rod head. This connecting rod head has a through-hole to allow an eccentric body 28 to be transversely inserted with the interposition of a bush 30. This eccentric body 28 has, on the two opposite sides, a hollow socket head 29 to receive a control socket wrench.

A manually rotatable ring nut 35, through which the eccentric body 28 passes as well, encloses the head of the interconnection pin 24. In particular, this ring nut 35 has a central slot into which the head of the interconnection pin 24 fits perfectly and a central hole through which the shank of the interconnection pin 24 passes.

It should be noted that the rotation of the eccentric body 28 in the ring nut 35 allows it to be locked and at the same time allows the second coupling element 31 to be pressed against the first two-seat coupling element 21, thus defining a relative locking between the various elements of which the clamp 20 is composed.

A washer 32 through which the interconnection pin 24 passes, is inserted between the ring nut 35 and the upper jaw 22 of the first two-seat coupling element 21.

The clamp 20 can have a slack configuration in which the jaws of the coupling elements 21, 31 are not fastened and the first two-seat coupling element 21 is rotating with respect to the second coupling element 31 around the main axis of rotation x'. In this slack configuration, therefore, a degree of rotational freedom is defined that allows the first two-seat coupling element 21 and of the second coupling element 31 to be positioned properly relative to each other. In alternative, the clamp 20 can have a locked configuration in which the jaws are fastened and the two coupling elements 21, 31 are integral with one other.

The manual fastening of the fastening ring nut 35 allows the whole clamp 20 to be rapidly pre-closed with no need to use a wrench. This operation brings the clamp 20 from the slack configuration to a temporary locked configuration, which ensures the fastening of the jaws and the relative locking of the two coupling elements, but does not ensure the rigidity and stability over time of these conditions.

Then, in order to change to a definitive locked configuration, in which rigidity and stability over time are ensured, it is necessary to rotate the eccentric body 28 by means of a control socket wrench.

The clamp according to the second embodiment has several advantages, such as:
    the use of a single clamp to connect two rods or a rod to an endosseous pin;
    the presence of a degree of rotational freedom for an easy relative positioning of the coupling elements;
    the option of manual pre-closure;
    the possibility to perform the fastening by a single rapid movement of the control wrench;
    the compatibility with MRI techniques.

Figure 8:
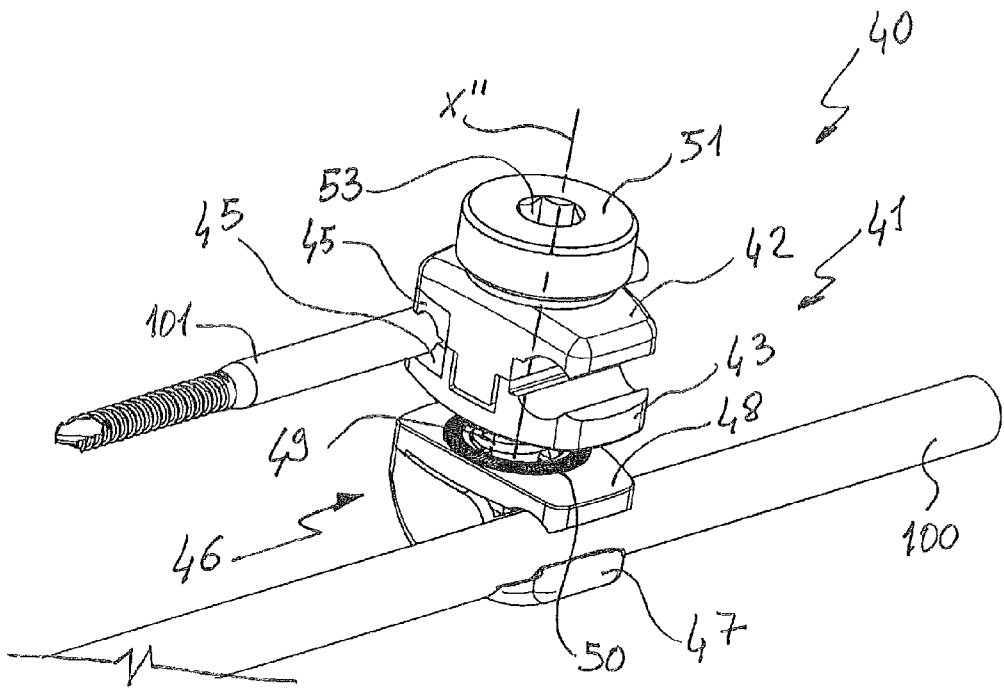
FIGS. 8 and 9 are respective axonometric views of a clamp according to a third embodiment of the present invention.
Figure 9:
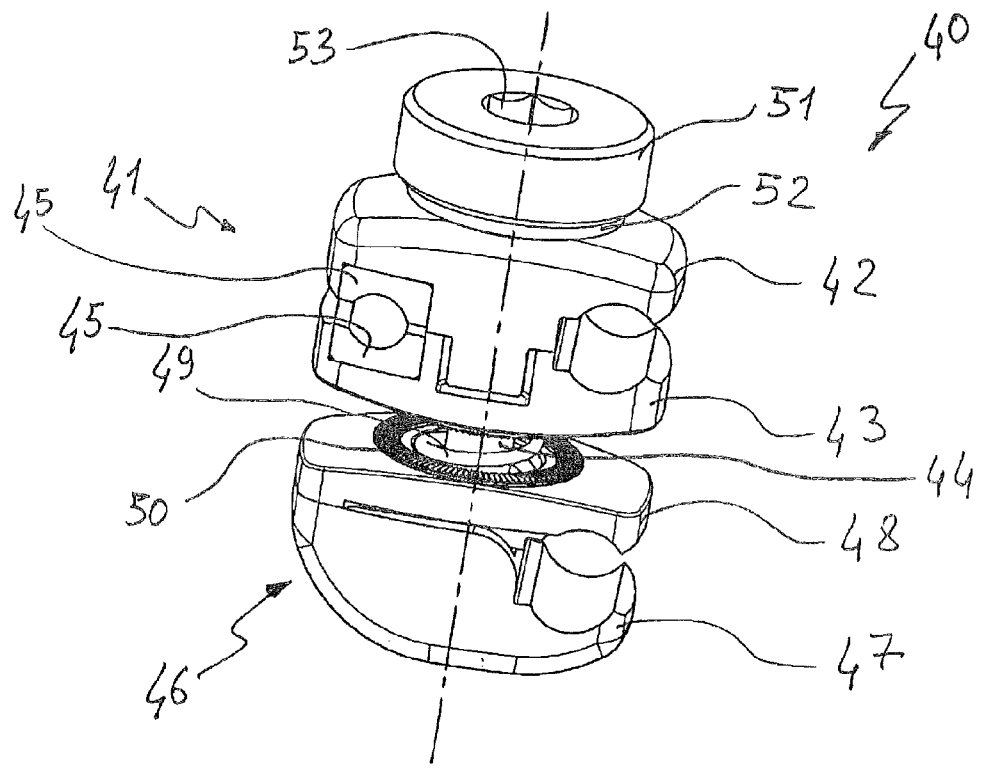
Figure 10:
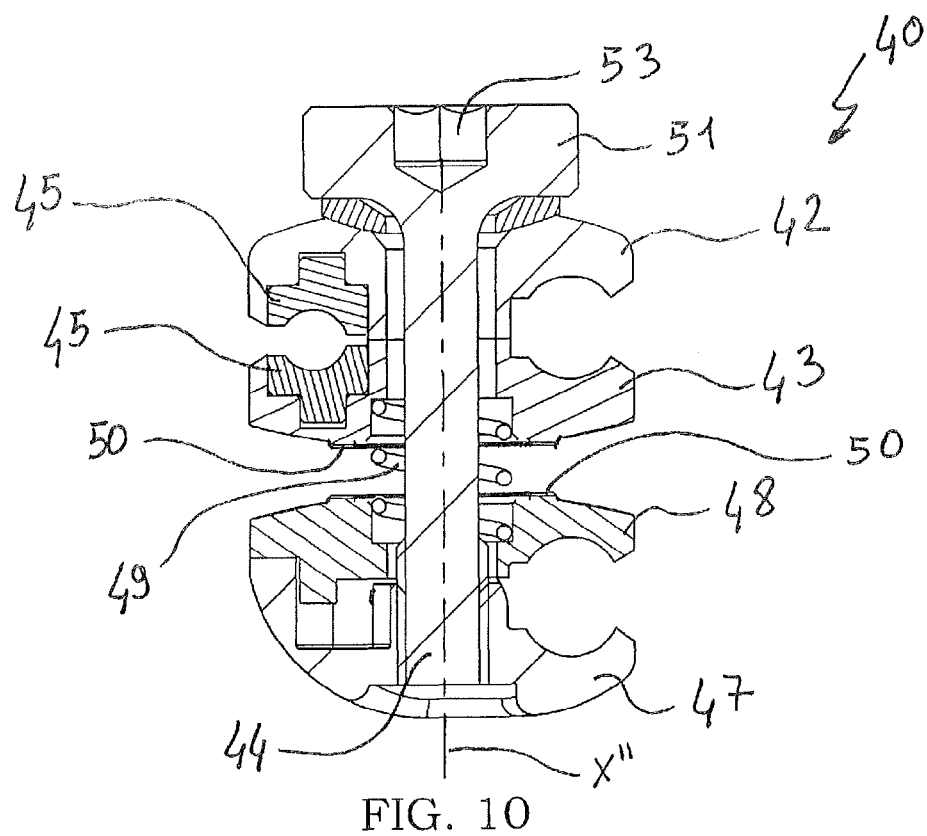
FIG. 10 is a sectional view along a vertical central plane of the clamp of FIGS. 8 and 9.

According to a third embodiment of the present invention, FIGS. 8-10 show a third clamp, globally indicated with 40, suitable to be used for the treatment of upper limbs, such as wrist, shoulder, hands.

The third clamp comprises a first two-seat coupling element 41 comprising an upper jaw 42 and a lower jaw 43, both provided with a central through-hole to allow an interconnection pin 44 orientated along a main axis of rotation x" to pass through.

The two-seat coupling element 41 has, next to the central hole and opposite to each other, open C-shaped seats to respectively house an endosseous pin 101 and a rod. It is also possible to modify the dimensions of these seats so that both are able to house an endosseous pin.

The open seats are therefore placed in an eccentric and orthogonal manner with respect to the main axis of rotation x".

An insert 45 is provided between the upper jaw 42 and the lower jaw 43 on the jaw portion that is intended to house the endosseous pin.

This insert is made of a different material than the material being used to realize the coupling element 41, in particular a non-conductive material, when the coupling element 41 is preferably made of steel.

More particularly, it is preferable that this insert 45 is made of a radiotransparent material that is MRI-compatible.

The third clamp 40 according to the present invention further comprises a second coupling element 46 having a lower jaw 47 and an upper jaw 48.

This second coupling element has a single opening for clamping a rod 100 between the jaws.

These lower 47 and upper 48 jaws of the second coupling element 41 of the third clamp 40 also have a central through-hole to allow the interconnection pin 44 to pass through.

This interconnection pin 44 has at its free end a threading that matches a corresponding internal threading that is present at least partially in the through-hole of the lower jaw 47 of the second coupling element 46.

In this manner the first two-seat coupling element 41 is rotatably mounted with respect to the interconnection pin 44, while the second coupling element 46 is rotatably constrained to the interconnection pin 44 to which it is screwed by means of its own lower jaw 47.

Basically the lower jaw 47 functions like a nut into which the entire third clamp 40 can be screwed.

A spring 49 is inserted between the first two-seat coupling element 41 and the second coupling element 46 around the interconnection pin 44. This spring 49 is compressed between the lower jaw 43 of the first two-seat coupling element 41 and the upper jaw 48 of the second coupling element 46, and concealingly housed in impressions on the opposite surfaces of these jaws. The spring 49 defines a spring-loaded fastening force exerted by the jaws on the elements inserted into the seats of the coupling elements before locking the clamp.

In order to avoid sliding during the usual assembly operations, respective anti-rotation means 50 are present on the surface of the upper jaw 48 of the second coupling element 46 and on the surface of the lower jaw 43 of the first coupling element 41; in the example these means are formed integrally with the body of the piece itself to which it is fixed and they comprise a plurality of radially oriented grooves on a crown placed around the central hole.

The end of the interconnection pin 44 opposite the one that is screwed on the second coupling element 46 has an expansion that is shaped like a planar fastening ring nut 51 that can be operated manually from the outside. In the middle of its free surface this fastening ring nut 51 has a socket hollow 53 to receive a control socket wrench.

A washer 52 through which the interconnection pin 44 passes, is inserted between the fastening ring nut 51 of the interconnection pin 44 and the upper jaw 42 of the first two-seat coupling element 41.

The third clamp 40 can have a slack configuration in which the jaws of the two coupling elements 41, 46 are not fastened and the first two-seat coupling element 21 is rotatable with respect to the second coupling element 46 around the main axis of rotation x". In this slack configuration therefore a degree of rotational freedom is defined that allows the first two-seat coupling element 41 and the second coupling element 46 to be positioned properly relative to each other. In alternative, the clamp 40 can have a locked configuration in which the two coupling elements 41, 46 are integral with one other and their jaws are fastened.

The manual fastening of the fastening ring nut 51 allows the whole clamp 40 to be rapidly pre-closed with no need to use a control socket wrench. This operation brings the clamp 40 from the slack configuration to a temporary locked configuration, which ensures the fastening of the jaws and the relative locking of the two coupling elements, but does not ensure the rigidity and stability over time of these conditions.

Then, in order to change to a definitive locked configuration, in which rigidity and stability over time are ensured, it is necessary to insert a control socket wrench into the socket hollow 53 of the fastening ring nut 51 and to fasten it by means of this tool.

The clamp according to the third embodiment has several advantages, such as:
    the use of a single clamp to connect two rods or a rod to an endosseous pin;
    the presence of a degree of rotational freedom for an easy relative positioning of the coupling elements;
    the option of manual pre-closure;
    the compatibility with MRI techniques.

Figure 11:
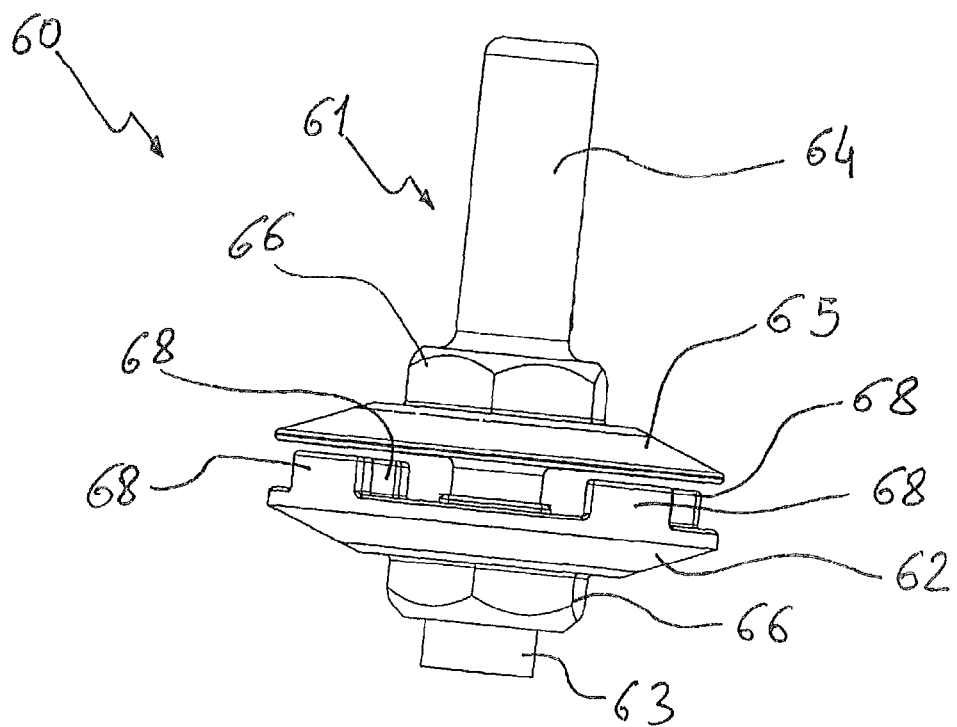
FIG. 11 is an axonometric view of an element of an external fixation system according to the present invention.
Figure 12:
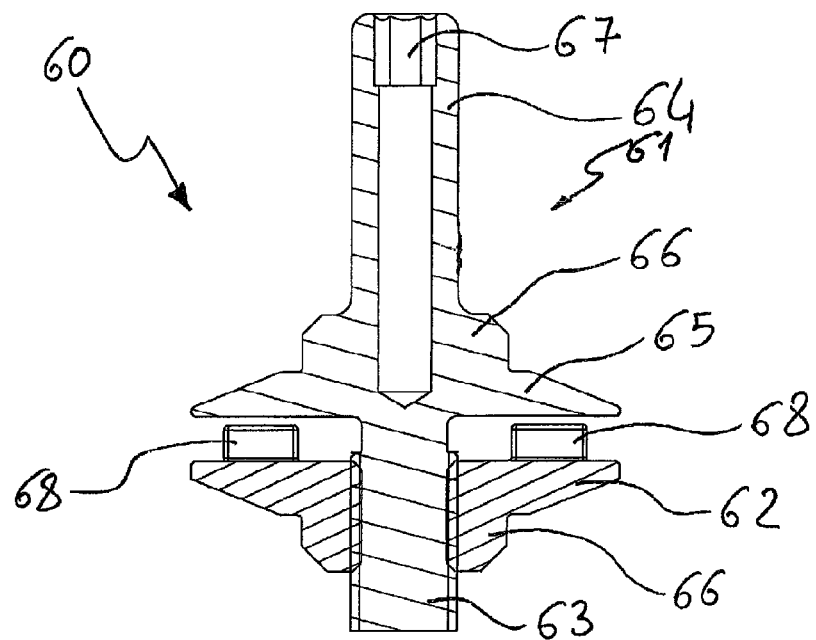
FIG. 12 is a sectional view, taken along a vertical central plane, of the element of FIG. 11.
Figure 13:
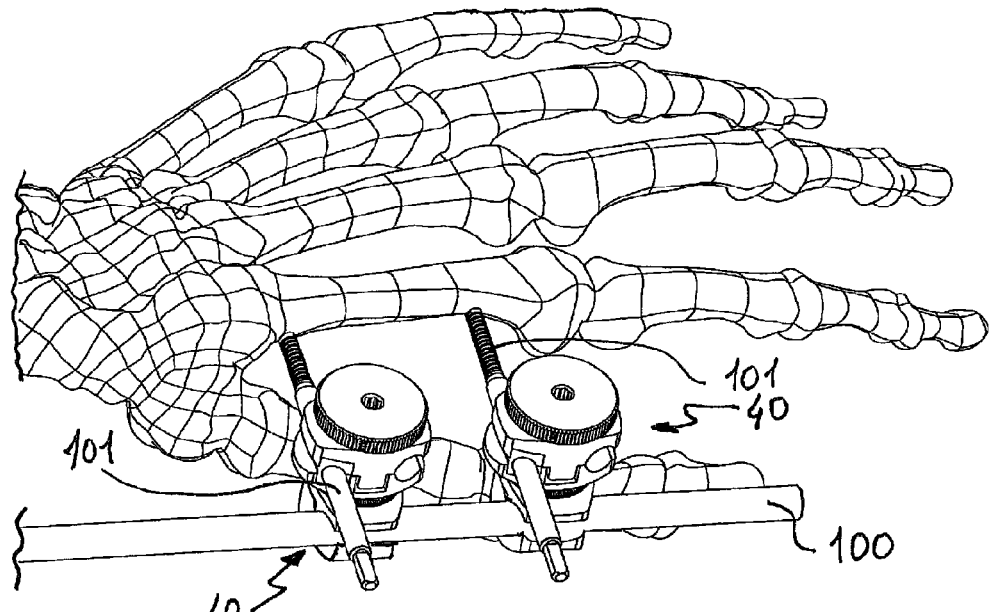
FIG. 13 is an axonometric view of an external fixation system according to the present invention applied to a first bone site of a patient.
Figure 14:
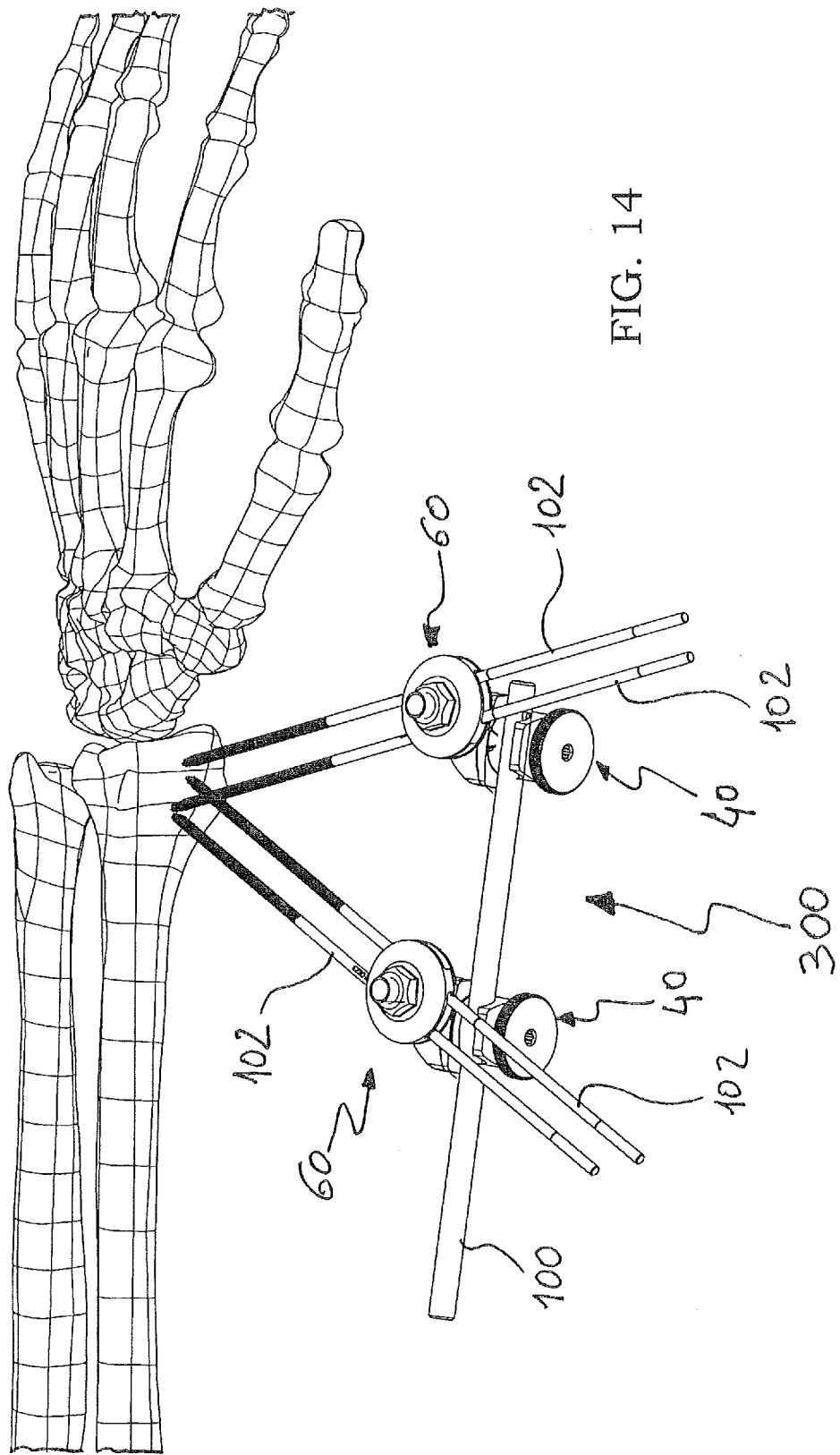
FIG. 14 is an axonometric view of an external fixation system according to the present invention applied to a second bone site of a patient.

The modular external fixation system 200, 300 according to the present invention, shown in FIGS. 13 and 14, can comprise one or more of the above-described clamps 1, 20, 40; moreover it can comprise a wire-carrier element 60 of the type shown in the attached FIGS. 11-12.

This wire-carrier element 60, which is particularly useful in fixation systems for bone sites of the wrist and shoulder, allows one or two Kirschner wires to be supported or alternatively as many screws 102 of reduced diameter (D=2.5 mm), partially or fully threaded.

The wire-carrier element 60 comprises a shank 61 and a fastening plate 62.

The main shank has a threaded portion 63, onto which said fastening plate 62 is screwed, and a non-threaded gripping portion 64; the two portions are divided by an abutting plate 65.

The fastening plate 62 has on its surface turned towards the abutting plate 65, when in use, four peripheral teeth 68, equiangularly spaced along the circumference of said plate.

When screwing the fastening plate 62 onto the threaded portion 63 of the shank 61, the four peripheral teeth 68 abut against a flat surface of the abutting plate 65, thus defining wire seats in collaboration with the shank 61 portion connecting the two plates.

Both the shank 61 and the fastening plate 62 comprise hexagonally shaped portions 66 on the external surface of the fastening/abutting plates for the insertion of a control wrench. The shank 61 also comprises a hexagonal hollow 67 located at the end of its gripping portion 64.

In order to insert a wire or a screw in the wire-carrier element 60, the wire or the screw is inserted in the channel defined by two peripheral teeth 68 on one side and by the shank 61 on the other side; a second wire or a second screw is then inserted in the channel defined on the other side of the shank by the peripheral teeth 68 opposite the first ones. A pair of parallel wires or screws can thus be associated to the wire-carrier element 60.

In order to associate the wire-carrier element 60 to the rest of the external fixation system, it is sufficient to lock its gripping portion 64 inside a coupling element of one of the system clamps.

The wire-carrier element described above has several advantages, such as:
- the possibility to use a normal clamp to connect rods or endosseous pins to Kirschner wires or screws of limited diameter;
- the possibility of an easy relative positioning of the elements to be connected;
- the secure fixing of wires or screws locked by the wire-carrier element;
- the great structural simplicity of the wire-carrier element, which consists of only two components.

Modular external fixation systems 200, 300 according to the present invention, which can be seen in two alternative embodiments in FIGS. 13 and 14, comprise, in addition to the above-described innovative components, rods 100 and endosseous pins 101, 102 of the known type.

The invention claimed is:

1. A clamp for an orthopaedic external fixation system comprising:
   a first coupling element, comprising a pair of opposite jaws together defining one or more seats able to house at least a first component of the orthopaedic external fixation system;
   a second coupling element, comprising a pair of opposite jaws together defining one or more seats able to house at least a second component of the orthopaedic external fixation system;
   an interconnection pin that passes through and connects the first and second coupling elements along a main axis of rotation;
   fastening means arranged to bring the clamp from a slack configuration, in which the first and second coupling elements are relatively rotatable at least along the main axis of rotation, to a locked configuration, in which the first and second coupling elements are relatively integral with each other;
   wherein said fastening means comprise:
   temporary fastening means, manually operable, arranged to temporarily bring the clamp in the locked configuration; and
   definitive fastening means, operable by means of a fastening tool, arranged to definitively bring the clamp in the locked configuration;
   wherein the interconnection pin passes through both single jaws of at least one of the pairs of jaws, said pair of jaws as a result not being fastened in the slack configuration of the clamp and fastened in the locked configuration of the clamp; and
   wherein the clamp comprises a spring interposed between the first and second coupling elements.

2. The clamp according to claim 1, wherein said temporary fastening means comprise a fastening ring nut arranged to fasten together the first and second coupling elements along the interconnection pin.

3. The clamp according to claim 2, wherein said fastening ring nut has a cylindrical peripheral handling surface.

4. The clamp according to claim 3, wherein said cylindrical peripheral handling surface is knurled.

5. The clamp according to claim 4, wherein said fastening ring nut engages a threaded end of the interconnection pin, the opposite end of said interconnection pin being constrained to the first coupling element, the second coupling element being interposed between the fastening ring nut and the first coupling element.

6. The clamp according to claim 4, wherein said fastening ring nut is axially constrained to an end of the interconnection pin, the opposite end being threaded and engaging an at least partially threaded hole of the second coupling element, said first coupling element being interposed between the fastening ring nut and the second coupling element.

7. The clamp according to claim 6, wherein said fastening ring nut defines a fastening head that is integral with the interconnection pin, said definitive fastening means comprising a hollow of said head intended to allow it to be coupled with a fastening tool.

8. The clamp according to claim 6, wherein said fastening ring nut encloses a connecting rod head of the interconnection pin, said definitive locking means comprising an eccentric body, rotatably mounted on the fastening ring nut, that passes through said connecting rod head along an axis that is perpendicular to the main axis of rotation, the rotation of said eccentric body with respect to the fastening ring nut promoting a translation of the end of the interconnection pin engaged in the second coupling element towards the fastening ring nut.

9. The clamp according to claim 2, wherein said definitive fastening means comprise an eccentric body, rotatably mounted on a hinging body that is axially integral with either one of the first or of the second coupling elements, said eccentric body passing through a connecting rod head of the interconnection pin along an axis that is perpendicular to the main axis of rotation, the opposite end of said interconnection pin being constrained to the other between the first and second coupling elements, the rotation of said eccentric body with respect to the hinging body promoting a translation of the opposite end of the interconnection pin towards said hinging body and as a result to relatively bring the two coupling elements nearer each other.

10. The clamp according to claim 9, wherein said fastening ring nut abuts against the outermost jaw of the second coupling element, said hinging body corresponding to the first coupling element, the end of the interconnection pin opposite the connecting rod head being threaded and constrained by screwing to the fastening ring nut.

11. The clamp according to claim 10, wherein said eccentric body hinges the first coupling element to the interconnection pin along a secondary axis of rotation, defining a second degree of rotational freedom between the first coupling element and the second coupling element in the slack configuration of the clamp.

12. The clamp according to claim 11, wherein said eccentric body is hinged on a base portion developing towards the second coupling element as a protuberance of the innermost jaw of the first coupling element.

13. The clamp according to claim 12, wherein a central joint is placed between the base portion and the second coupling element, through which the interconnection pin passes, said central joint presenting a sliding face along a concave periphery of the base portion and a flat face intended to couple with a surface of the internal jaw of the coupling element.

14. An orthopaedic external fixation system comprising a clamp for an orthopaedic external fixation system comprising:
- a first coupling element, comprising a pair of opposite jaws together defining one or more seats able to house at least a first component of the orthopaedic external fixation system;
- a second coupling element, comprising a pair of opposite jaws together defining one or more seats able to house at least a second component of the orthopaedic external fixation system;
- an interconnection pin that passes through and connects the first and second coupling elements along a main axis of rotation;
- fastening means arranged to bring the clamp from a slack configuration, in which the first and second coupling elements are relatively rotatable at least along the main axis of rotation, to a locked configuration, in which the first and second coupling elements are relatively integral with each other;

wherein said fastening means comprise:
- temporary fastening means, manually operable, arranged to temporarily bring the clamp in the locked configuration;
- definitive fastening means, operable by means of a fastening tool, arranged to definitively bring the clamp in the locked configuration, and
- comprising at least a wire-carrier element, arranged to allow at least a Kirschner wire or other fixator of limited diameter to be fixed to a system clamp,
wherein said wire-carrier element comprises a shank with a threaded portion whereon a fastening plate is screwed until it abuts against an abutting plate that is integral with the shank.

15. The orthopaedic external fixation system according to claim 14, wherein said shank comprises a gripping portion intended to be locked between jaws of the system clamp.

16. The orthopaedic external fixation system according to claim 15, wherein the fastening plate has, on one of its faces turned towards the abutting plate, four peripheral teeth, equiangularly spaced along the circumference of said plate and arranged to abut against a flat surface of the abutting plate, defining, in collaboration with the shank portion comprised between the two plates, a seat for a Kirschner wire or other fixator of limited diameter.

* * * * *